United States Patent [19]

Simcox et al.

[11] Patent Number: 6,054,307

[45] Date of Patent: *Apr. 25, 2000

[54] OCTANUCLEOTIDE RESTRICTION ENDONUCLEASE, SRF I, AND METHOD FOR PRODUCING SAME

[75] Inventors: Timothy G. Simcox; Mary E. Simcox, both of Del Mar, Calif.

[73] Assignee: Stratagene, La Jolla, Calif.

[*] Notice: This patent is subject to a terminal disclaimer.

[21] Appl. No.: 08/932,445

[22] Filed: Sep. 19, 1997

Related U.S. Application Data

[63] Continuation of application No. 08/652,857, May 23, 1996, abandoned, which is a continuation of application No. 08/222,203, Apr. 1, 1994, abandoned, which is a continuation-in-part of application No. 08/065,078, May 20, 1993, Pat. No. 5,300,432, which is a continuation of application No. 07/778,772, Oct. 18, 1991, abandoned.

[51] Int. Cl.[7] .................................................. C21N 9/22
[52] U.S. Cl. ............................................................ 435/199
[58] Field of Search ................................................ 435/199

[56] References Cited

U.S. PATENT DOCUMENTS

| 5,278,060 | 1/1994 | Morgan et al. | 435/199 |
| 5,300,432 | 4/1994 | Simcox et al. | 435/199 |
| 5,418,150 | 5/1995 | Topal et al. | 435/93.53 |

OTHER PUBLICATIONS

Kotani, et al. *Nucleic Acids Res.*, 18:5637–5640 (1990).
Lunnen, K.D. et al. *Gene*, 74: 25–32 (1988).
Nelson, et al. *Nucleic Acids Res.*, 18:2061–2064 (1990).
Roberts, *Nucleic Acids Res.*, 18:2331–2365 (1990).
Roberts, et al. *Nucleic Acids Res.*, 20:2167–2180 (1992).
Tautz, et al. *Nucleic Acid Res.*, 18:3087 (1990).
Simcox, et al. *Gene*, 109: 121–123 (1991).
Kessler, et al. *Gene*, 92: 241–245 (1990).

*Primary Examiner*—Charles L. Patterson, Jr.
*Attorney, Agent, or Firm*—Finnegan, Henderson, Farabow, Garrett & Dunner, L.L.P.

[57] ABSTRACT

This invention provides restriction endonuclease Srf I, which is capable of recognizing the eight nucleotide base palindromic sequence shown below on a double stranded DNA molecule and cleaving the DNA chain at the asterisk-marked position resulting in blunt ends

```
5'GCCC*GGGC3'
3'CGGG*CCCG5'
```

(wherein G and C respectively represent the nucleotides guanine and cytosine). The restriction endonuclease is produced by culturing Streptomyces rf in a culture medium and recovering it from the culture.

The invention also provides polynucleotides encoding Srf I. Another aspect of this invention is to provide for the recombinant DNA production of Srf I. Another aspect of the invention is to provide for non-naturally occurring variants of Srf I, as well as the polynucleotides encoding these proteins.

3 Claims, 3 Drawing Sheets

FIG.4

```
27205    5'-CAGCG CCATTATGAG CAAGGAAATT CCCACGCCCT    27239
         ACATGTGGAG TTACCAGCCA CAAATGGGAC TTGCGGCTGG    27279
         AGCTGCCCAA GACTACTCAA CCCGAATAAA CTACATGAGC    27319
         GCGGGACCCC ACATGATATC CCGGGTCAAC GGAATCCGCG    27359
         CCCACCGAAA CCGAATTCTC CTCGAACAGG CGGCTATTAC    27399
         CACCACACCT CGTAATAACC TTAATCCCCG TAGTTGGCCC    27439
         GCTGCCCTGG TGTACCAGGA AAGTCCCGCT CCCACCACTG    27479
         TGGTACTTCC CAGAGACGCC CAGGCCGAGG TTCAGATGAC    27519
         TAACTCAGGG GCGCAGCTTG CGGGCGGCTT TCGTCACAGG    27559
         GTGCGGTCGC CCGGGCAGGG TATAACTCAC CTGAAAATCA    27599
         GAGGGCGAGG TATTCAGCTC AACGACGAGT CGGTGAGCTC    27639
         CTCTCTTGGT CTCCGTCCGG ACGGGACATT TCAGATCGGC    27679
         GGCGCTGGCC GCTCTTCATT TACGCCCCGT CAGGCGATCC    27719
         TAACTCTGCA GACCTCGTCC TCGGAGCCGC GCTCCGGAGG    27759
         CATTGGAACT CTACAATTTA TTGAGGAGTT CGTGCCTTCG    27799
         GTTTACTTCA ACCCCTTTTC TGGACCTCCC GGCCACTACC    27839
         CGGACCAGTT TATTCCCAAC TTTGACGCGG TGAAAGACTC    27879
         GGCGGACGGC TACGACTGAA TGACCAGTGG AG-3'          27911
```

OCTANUCLEOTIDE RESTRICTION ENDONUCLEASE, SRF I, AND METHOD FOR PRODUCING SAME

RELATED APPLICATIONS

This application is a continuation of U.S. patent application Ser. No. 08/652,857, filed May 23, 1996, now abandoned, which is a continuation of U.S. patent application Ser. No. 08/222,203, filed Apr. 1, 1994, now abandoned, which is a continuation-in-part of U.S. patent application Ser. No. 08/065,078, filed May 20, 1993, now U.S. Pat. No. 5,300,432, which issued on Apr. 5, 1994, which is a continuation of U.S. patent application Ser. No. 07/778,772, filed Oct. 18, 1991, now abandoned.

TECHNICAL FIELD

This invention provides restriction endonuclease, Srf I, capable of recognizing an eight nucleotide base palindromic sequence on a double-stranded DNA molecule and cleaving the DNA chain to result in blunt ends. The restriction endonuclease is produced by culturing Streptomyces rf in a culture medium and recovering it from the culture.

BACKGROUND

Restriction endonucleases are capable of recognizing a specific sequence of bases of a deoxyribonucleic acid (DNA) molecule and of enzymatically cleaving in a process termed restriction the double-stranded DNA chain at specific sites. Different restriction endonucleases have an affinity for different recognition sequences. When they are purified away from other contaminating bacterial components, restriction endonucleases can be used in the laboratory to cut DNA molecules into specific fragments. This property enables DNA molecules to be uniquely identified and to be fractionated into their constituent genes. Restriction endonucleases, thus, allow the researcher to manipulate the DNA molecule and analyze the resulting construction.

Bacteria usually possess a limited number of restriction endonucleases per species. The endonucleases are named according to the bacteria from which they are derived. For example, the species *Proteus vulgaris* contains two known restriction endonucleases, named Pvu I and Pvu II. These restriction enzymes recognize and cleave the sequences CGATCG and CAGCTG respectively. *E. coli* RY13, on the other hand synthesizes only one enzyme, Eco RI which recognizes the sequence GAATTC.

More than 1000 class-11 restriction endonucleases have been identified. See, Kessler et al., 47:1–153 (1986) and Roberts, *Nuc. Acids Res.* 17:347–387 (1989) and Kessler et al., Gene, 92:1–248 (1990). The majority of these enzymes recognize four or six base pair palindromic sequences. Thus far, only eight restriction endonucleases with octanucleotide recognition sequences have been found: Asc I (5'-GG/CGCGCC-3', New England Biolabs, Beverly, Mass.); Fse I (5'-GGCCGG/CC-3', Nelson et al, *Nucl. Acids Res.*, 18:2061–2064 (1990); Not I (5'-GC/GGCCGC-3', Qiang et al., *Nucl. Acids Res.*, 12:4507–4515 (1984); Pac I (5'-TTAAT/TAA-3', Polisson et al., unpublished observations; Sfi 1 (5'-GGCCNNNN/NGGCC-3', where N is either A, C, G or T, Qiang et al., supra; Sgr AI (5'-CR/CCGGYA-3', where R is either A or G and Y is either C or T, Tantz et al., *Nucl. Acids Res.*, 18:3087–3089 (1990); Sse 8287 I (5'-CCTGCA/GG-3', Kotani et al., *Nucl. Acids Res.*, 18:5637–5640 (1990); and Swa I (5'-ATTTAAAT-3', Boehringer Mannheim Biochemicals, Indianapolis, Ind.).

Restriction enzymes having these specificities are especially useful for mammalian genome analysis. The purification and characterization of a novel octanucleotide restriction endonuclease, designated Srf I, is the subject of this invention. The isolation of polynucleotide encoding Srf I and a Srf I methylase is also the subject of this invention.

BRIEF DESCRIPTION OF THE INVENTION

The present invention provides a new restriction endonuclease with specificity for an Octanucleotide palindromic sequence, the cleavage of which results in DNA having blunt ends. A preferred method for a culture of Streptomyces rf (ATCC Budapest Treaty Deposit Accession Number 55215) is also Provided. The Streptomyces rf strain was deposited with the American Type Culture Collection (ATCC Bethesda, Md.) on Aug. 1, 1991 by the depositor (Stratagene, La Jolla, Calif.) and has been assigned a deposit accession number that is available from the ATCC.

The invention, thus, relates to a new restriction endonuclease, Srf I, having the following properties:

(a) Substrate specificity—The endonuclease recognizes the palindromic nucleotide base sequence as shown below for each respective strand on a double-stranded DNA molecule and cleaves the DNA at the asterisk-marked position to result in DNA having blunt ends

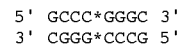

(wherein C and G respectively represent the nucleotides, cytosine and guanine);

(b) Optimal pH range—7.0 to 8.0; Preferred pH is 7.6;

(c) Stable pH range—6.0 to 8.5;

(d) Optimal temperature—37 degrees Celsius (37° C.);

(e) Optimal salt concentration range—50 to 100 mM potassium acetate is preferred; the endonuclease activity is also maintained in sodium chloride concentrations up to 50 mM, but is retarded at higher levels and completely inhibited in 150 mM sodium chloride;

(f) Optimal magnesium acetate concentration range—the endonuclease activity is maximal in 5 to 10 mM of magnesium acetate; the activity is also maintained in 10 mM magnesium chloride;

(g) Optimal buffer concentration—25 mM Tris-acetate; the endonuclease activity is also maintained in a Tris-HCl buffer ranging in concentration from 10 to 25 mM.

This invention also relates to the method for producing the novel restriction endonuclease, Srf I, which comprises growing a Streptomyces rf culture corresponding to that deposited under ATCC Accession Number 55215 and capable of producing Srf I in a culture medium, and recovering the Srf I thus formed from the culture.

This invention also relates to the isolation of polynucleotides encoding Srf I and Srf I methylase. Another aspect of this invention is to provide for the recombinant DNA production of Srf I. Another aspect of the invention is to provide for non-naturally occurring variants of Srf I, as well as the polynucleotides encoding these proteins.

BRIEF DESCRIPTION OF THE DRAWINGS

FIG. 4 illustrates the nucleotide sequence of a portion of the Adenovirus-2 gene beginning at nucleotide position 27205 and ending at 27911. The same sequence-is also listed in the Sequence as SEQ ID NO 1 where the corresponding nucleotides are listed beginning at 1 and ending at 707.

DETAILED DESCRIPTION OF THE INVENTION

Figure 1:
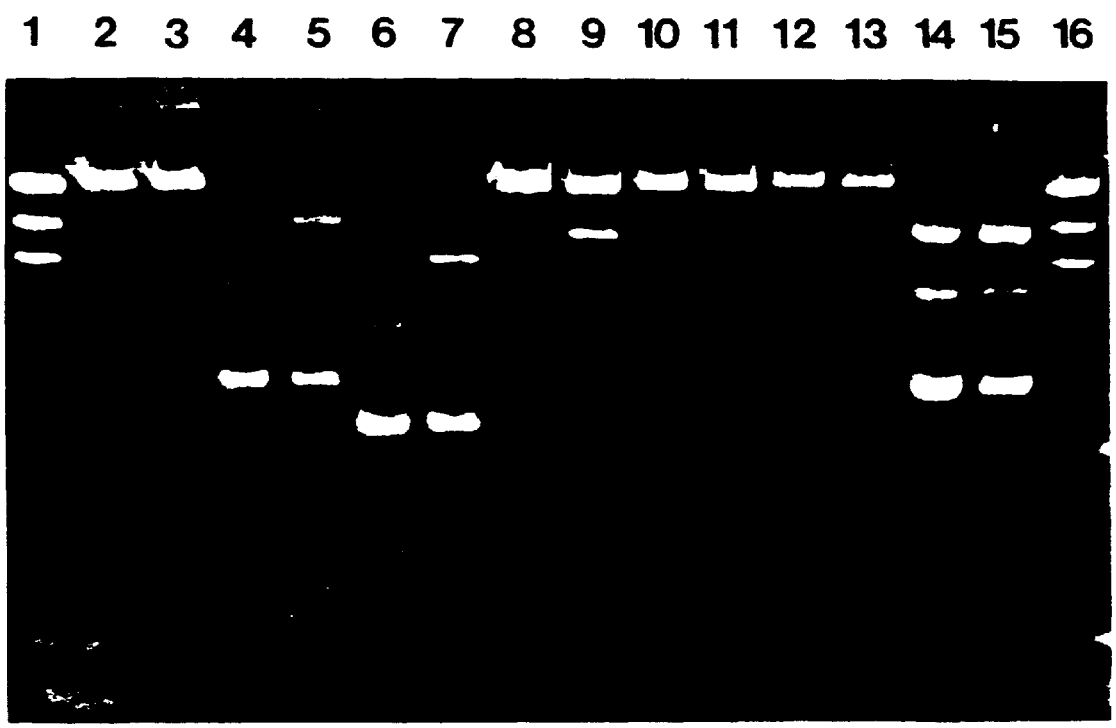
FIG. 1 illustrates the cleavage activity of Srf I on the DNA substrate Adenovirus-2 (Ad-2) which results in producing two fragments of 27,571 and 8,366 base pairs long as shown in Lane 9. Control undigested Adenovirus-2 is in Lane 8. Srf I failed to cleave the DNA templates, phage lambda (dam-, dcm-), PhiX174, pBR322, T7, T5 and SV40. Each DNA substrate was electrophoresed on a 1% agarose gel in a pair-wise left and right arrangement to respectively compare undigested substrate to substrate maintained with Srf I. The lanes in FIG. 1 contain the following DNA: Lanes 1 and 16—Lambda Hind III molecular weight marker; Lanes 2 and 3—Lambda undigested Srf I treated; Lanes 4 and 5—PhiX174 undigested and Srf I treated; lanes 6 and 7—pBR322 undigested and Srf I treated; Lanes 8 and 9—Adenovirus-2 undigested and Srf I treated; Lanes 10 and 11—T7 undigested and Srf I treated; Lanes 12 and 13 T5 undigested and Srf I treated; and Lanes 14 and 15—SV40 undigested and Srf treated.

Any species of Streptomyces that is capable of producing Srf I can be used for the purpose of this invention. A typical example, Streptomyces rf has been deposited at the American Type Culture Collection (ATCC), Rockville, Md. under the Accession Number 55215. These can be grown in a jar fermentor by the usual method, and the grown microbial cells separated from the culture liquid by centrifugation.

Restriction endonuclease Srf I has the following properties:

(a) Substrate specificity—The endonuclease recognizes the palindromic nucleotide base sequence as shown below for each respective strand on a double-stranded DNA molecule and cleaves the DNA at the asterisk-marked position to result in DNA having blunt ends

```
5' GCCC*GGGC 3'
3' CGGG*CCCG 5'
```

(wherein C and G respectively represent the nucleotides, cytosine and guanine);

(b) Optimal pH range—7.0 to 8.0; preferred pH is 7.6;

(c) Stable pH range—6.0 to 8.5;

(d) Optimal temperature—37 degrees Celsius (37° C.);

(e) Optimal salt concentration range—50 to 100 mM potassium acetate is preferred; the endonuclease activity is also maintained in sodium chloride concentrations up to 50 mM, but is retarded at higher levels and completely inhibited in 150 mM sodium chloride;

(f) Optimal magnesium acetate concentration range—the endonuclease activity is maximal in 5 to 10 mM of magnesium acetate; the activity is also maintained in 10 mM magnesium chloride;

(g) Optimal buffer 'concentration—25 mM Tris-acetate; the endonuclease activity is also maintained in a Tris-HCl buffer ranging in concentration from 10 to 25 mM.

Srf I can be extracted and purified using known techniques commonly employed for restriction enzymes. The cultured cells are collected from their growth medium and dispersed in a suitable buffer. Subsequently, the cells are disrupted, typically by the application of one or a combination of shear force, osmotic pressure, ultrasound and the like, to permit extraction of the endonuclease by the buffer solution. After removal of cellular debris, such as by centrifugation, the supernatant is subjected to the as gel filtration, gel chromatography, ultrafiltration, electrophoretic mobility, ion exchange, dialysis, and the like, to separate and recover a protein with the above described characteristics from the other proteins present.

For instance, it is well known in the art that affinity chromatography on heparin-sepharose can be used to reproducibly isolate proteins from complex biological sources. Proteins in a solution are applied to a column containing an affinity matrix and subsequently eluted therefrom according to the salt ion concentration of a buffer passing through the column. Eluate fractions are collected and those containing the above-described restriction enzymes are recovered. After dialysis to remove excess salt, the partially purified Srf I isolate can be further purified, typically by a series of further chromatographic separations. Particularly useful are those utilizing Blue sepharose, Mono S FPLC and Mono Q FPLC, all obtainable from Pharmacia, Piscataway, N.J., and phosphocellulose available from Whatman Biosystems Limited, Maidstone, Kent, England.

The isolated Srf I is typically admixed in an aqueous solution, which can contain one or more of a pH buffering agent, reducing agent, ion-chelator, surfactant, stabilizing protein such as bovine serum albumin (BSA), and stabilizer such as glycerol. preferred aqueous compositions contain Srf I at a concentration of at least 1 unit/μl, more preferably at a concentration of at least 4 units/μl and most preferably at least 10 units/μl. Of course, concentrations at least as high as 15 units/μl 20 units/μl and 30 units/μl are also contemplated.

Isolation of Genes Encoding Srf I

As purified preparations of Srf I may be produced using the above described techniques, purified Srf I may be used to isolate polynucleotide sequences encoding Srf I. Polynucleotide sequences encoding Srf I may be isolated from any biological organism naturally producing Srf I, typically Streptomyces species, (Streptomyces rf strain ATCC deposit number 55215) being particularly preferred.

Many techniques are available for the cloning of restriction endonucleases and modification enzymes capable of specifically methylating nucleotide bases within the target sequences recognized by the corresponding restriction endonuclease, provided that compositions containing the purified restriction endonuclease activity of interest are available. These gene isolation techniques are described, among other places in U.S. Pat. Nos. 5,200,333; 5,139,942; 5,175,101; 5,147,794, and other patents describing the cloning of restriction endonuclease genes. Additionally, many techniques useful for the isolation of polynucleotide sequences encoding any polypeptide of interest that do not rely on the enzymatic activity of the polypeptide encoded by the polynucleotide to be isolated, may be applied to restriction endonucleases, including Srf I. The gene isolation techniques of general applicability are well known to the person of ordinary skill in the art and include such methods as the screening of genetic libraries, Srf I variants, Srf I isochizomers, and other restriction endonucleases inhibited by the methylation with oligonucleotide probes based on information derived from N-terminal sequencing of polypeptides of interest or the N-terminal sequencing of internal peptide fragments, and the screening of genetic libraries with antibodies specific for the polypeptides of interest. Detailed protocols for general techniques for the isolation of polynucleotide encoding polypeptides of interest based on having the purified polypeptide of interest can be found in, among other places, Sambrook et al. *Molecular Cloning; A Laboratory Manual, 2nd Ed.* Cold Spring Harbor Press, Cold Springs Harbor (1989), Ausubel et al., *Short Protocols in Molecular Biology 2nd edition*, Academic Press, San Diego (1992), Berger and Kimmel *Guide to Molecular Cloning techniques*; Academic Press, San Diego (1987), and the like.

The amino acid sequence of Srf I and the naturally occurring polynucleotide sequences encoding Srf I enable a person of ordinary skill in the art of molecular biology to design and construct a variety of related molecules having useful properties similar to Srf I and naturally occurring polynucleotides encoding a Srf I. In the case of polynucleotides, the degeneracy of the genetic code permits the person of ordinary skill in the art to produce numerous different polynucleotides encoding the same polypeptide, i.e., isocoding polynucleotides. The precise polynucleotide sequence produced may be selected so as to optimize expression in a particular host cell type, taking into account factors affecting expression such as codon frequency, potential mRNA secondary structures, methylation, and the like. The invention also provides a variety of polypeptides having the same restriction site recognition and cleavage activity as Srf I, but differing in one or more amino acid residues, so as to produce a Srf I variant polypeptide. Srf I variants may be produced and designed in a wide variety of ways. Srf I variants may be produced and designed by introducing mutations (either random or by design) into a polynucleotide sequence encoding Srf I, transforming the mutated Srf I encoding polynucleotide (operably linked to a suitable promoter) into a host cell, and subsequently assaying the host cell for the expression of Srf I restriction endonuclease activity. The identity of mutations in Srf I encoding polynucleotides introduced randomly, may be determined by sequencing the polynucleotide encoding the enzyme.

The invention also provides for the recombinant DNA expression of Srf I (as well as variants thereof). The recombinant expression of these enzyme may be achieved through standard recombinant DNA expression technology. Suitable recombinant DNA expression technology can be found, among other places, in Goeddel, et al., *Gene Expression Technology: Methods in Enzymology Volume* 185 Academic Press, San Diego (1991). The enzyme may be expressed in a wide range of host cells, including both eukaryotic and prokaryotic host cells. One advantage of providing the subject enzymes by recombinant DNA methodology is the production of increased amounts of enzyme from reduced amounts of cellular material.

Another advantage of the recombinant production of the enzymes is the ability to produce the enzyme free of certain contaminants. Srf I and Srf I variants produced by recombinant DNA techniques may be purified by procedures similar to the procedures described herein for the purification of non-recombinant Srf I. Guidance in devising and modifying enzyme purification procedures can be found, among other places in Deutscher *Guide to Protein Purification Methods in Enzymology—Volume* 182) Academic Press, San Diego (1990), Scopes *Protein Purification: Principles and Practice 3rd edition* Springer-Verlag, New York (1993), and the like.

EXAMPLES

The following examples are given to illustrate embodiments of the present invention as it is presently preferred in practice. It will be understood that these examples are illustrative of the invention and are not to be considered as limiting.

1. Preparation of Srf I Restriction Endonuclease a. Preparation of Crude Streptomyces Cell Extracts Eight Streptomyces bacterial strains were screened for endonuclease activities. All eight strains were separately maintained at 30 degrees Celsius (30° C.) in Streptomyces media, which contained 1% peptone, 0.1% yeast extract, 1% glucose, 10 millimolar (mM) Tris-HCl (Tris [hydroxymethyl]aminomethanehydrochloride) at pH 7.5, until the cells reached the late logarithmic phase of growth. Twenty grams of cells were obtained from each Streptomyces culture by centrifugation at 10,000 rpm for ten minutes in a Beckman JA20 centrifuge to form a cell pellet. Each pellet was separately resuspended in Buffer A (10 mM potassium phosphate ($KPO_4$), 10 mM beta-mercaptoethanol and 1 mM EDTA [ethylenediaminetetraacetic acid]) to form a cell suspension before passing through a Mouton-Gaulin press at 12,000 psi. The resultant slurries were maintained separately at less than 4° C. but above freezing during disruption and throughout further enzyme purification. For each strain screened, the salt concentration was increased to 0.3 M potassium chloride (KCl) and the suspension was then centrifuged for 1 hour at 12,000 rpm (Beckman) to pellet the cellular debris.

The resulting supernate containing the extracted (isolated) restriction endonucleases was diluted at a 1:3 ratio with Buffer A and applied onto a heparin sepharose column (1.5 cm×7 cm) (Pharmacia, Piscataway, N.J.) previously equilibrated with Buffer A containing 0.1 M KCl. A KCl gradient (0.1 M to 0.8 M) was used to elute Srf I activity immobilized on the column. One milliliter (ml) fractions were collected and DNA cleavage activity in the collected fractions was measured in an endonuclease assay as described below on the following DNA substrates: Phage Lambda (dam$^-$, dcm$^-$), Adenovirus-2, pBR322, PhiX174, T7, SV40 and T5.

b. Endonuclease Activity of Crude Streptomyces Extracts

Endonuclease activity was measured by admixture of 8, 4, 2 and 1 microliter(s) $\mu$l of each of the column fractions for each of the eight extracted Streptomyces strains prepared in Example 1a with 0.25 microgram ($\mu$g) of each of the following DNA substrates: Phage Lambda (dam$^-$, dcm$^-$) (Stratagene); Adenovirus-2 (Ad- 2) (Bethesda Research Laboratories, Gaithersburg, Md.) pBR322 as described by Bolivar et al., *Gene*, 2:95–116 (1977) (Stratagene); PhiX174 (Stratagene), T7 (Sigma Chemical, St. Louis, Mo.); SV40 (Sigma); and T5 (Sigma). The phage lambda DNA template was isolated from bacteriophage lambda C1859 ind/Sam 7 grown in *E. coli* strain JM110 (dam, dcm). The admixtures were diluted to 1× Universal Buffer (Stratagene) which was diluted from a 10× Universal Buffer stock solution of 250 mM Tris-acetate at pH 7.6, 1 M potassium acetate, 100 mM magnesium acetate, 5 mM beta-mercaptoethanol and 100 $\mu$g/ml of bovine serum albumin (BSA). The separate Streptomyces crude cell extracts-DNA substrate admixtures were maintained for 30 minutes at 37° C. to allow endonucleolytic cleavage activity to occur.

After the maintenance period, the substrate DNAs were separately admixed with gel-loading buffer and electrophoresed on a 1% agarose gel following procedures well known to one skilled in the art (Maniatis et al., *Molecular Biology: A Laboratory Manual 2nd Ed.*, Cold Spring Harbor Laboratory, (1989)) in order to visualize the restriction endonuclease cleavage products. Crude extracts from one strain of Streptomyces exhibited endonuclease activity on Adenovirus-2 DNA but not on any of the other DNA substrates evaluated. A restriction endonuclease with this limited cleavage specificity has not been described before this present invention. The Adenovirus-2 DNA was cleaved only in one place resulting in two fragments of 27,571 and 8,366 base pairs in length. The Streptomyces strain, from which the Adenovirus-2 DNA-cleaving restriction endonuclease was isolated, was then selected for further purification and characterization of the novel restriction endonuclease. The selected strain, designated Streptomyces rf has been deposited in accordance with the Budapest Treaty and has been assigned ATCC Accession Number 55215.

c. Purification of the Novel Streptomyces Restriction Endonuclease Srf I

To purify sufficient quantities of the novel restriction endonuclease, designated Srf I, described above for subsequent characterization assays, 600 grams of cells were harvested from a late log phase culture of the selected Streptomyces rf by centrifugation as described in Example 1a. The pelleted cells were then resuspended in Buffer B (10 mM Tris-HCl at pH 7.8, 10 beta-mercaptoethanol, 5 mM EDTA, 10 mM ammonium sulfate, 1% glycerol, 0.1% Triton X-100). After several passes through a Mouton-Gaulin press at 12,000 psi at non-freezing temperatures less than 4° C., the resultant cell slurry was brought to 0.3 M KCl and centrifuged at 12,000 rpm in a Beckman centrifuge equipped with a JA14 rotor for 2 hours to pellet cellular debris. The isolated endonuclease (supernate) was recovered and diluted in a 1:3 ratio with Buffer B.

The diluted supernate was then applied onto a heparin sepharose column (5×10 cm, previously equilibrated with Buffer B containing 0.1 M KCl). The column was washed with two column volumes of 0.1 M KCl in Buffer B to remove any unbound contaminants. The immobilized Srf I was then eluted using a 0.1 to 0.8 M KCl gradient in Buffer B. Fractions containing assayable restriction endonuclease activity as determined in Example 1b were collected, pooled and dialyzed against Buffer C (10 mM Tris-HCl at pH 8.0, 10 mM beta-mercaptoethanol, 5 mM EDTA, 1% Glycerol, 0.1% Triton X-100, 10 mM ammonium sulfate and 190 mM KCl).

After dialysis and titration, the partially purified restriction endonuclease Srf I was applied onto a Blue sepharose column (25×15 cm) (Pharmacia) previously equilibrated with Buffer C. The column was washed with two column volumes of Buffer C to remove any unbound contaminants and then the immobilized restriction endonuclease was eluted with a KCl gradient (0.19 M to 1.5 M). Fractions were collected into tubes pre-loaded with 50 $\mu$g/ml BSA and assayed for restriction enzyme activity as described in Example 1b. The fractions were also assayed for the presence of exonucleases and DNA binding proteins following methods familiar to one skilled in the art.

Fractions containing Srf I endonucleolytic activity were pooled and dialyzed against Buffer B containing 0.1 M KCl. After centrifuging the light precipitate at 12,000 rpm for 20 minutes in a JA14 rotor, the resultant supernate was applied to a heparin sepharose column (1.5×10 cm), previously equilibrated with Buffer B made in 0.1 M KCl. The column was washed with 2 column volumes of equilibration buffer to remove any unbound contaminants and Srf I was then eluted using a 0.1 to 0.8 M KCl gradient. Eluted fractions were collected into tubes pre-loaded with 100 $\mu$g/ml BSA. Endonuclease and exonuclease assays were performed on these column fractions and the endonuclease component was isolated from 90% of the exonuclease activity.

The resultant pooled partially purified restriction endonuclease was then dialyzed against Buffer D (20 mM KPO$_4$, pH 7.0, 10 mM beta-mercaptoethanol, 5 mM EDTA, 40 mM KCl, 10 mM ammonium sulfate, 5% glycerol, 0.1% Triton X-100) and applied onto a Mono S (strong cationic exchanger based on monodisperse hydrophilic polymer particles, Pharmacia) FPLC column (Pharmacia). Following a two column volume wash, the endonuclease was eluted with a KCl gradient (0.04 to 0.5 M KCl) into collection vials containing 100 $\mu$g/ml BSA. Srf I eluted at approximately 0.25 M KCl, prior to a second restriction enzyme, designated Srf II, the activity of which was distinct from Srf I. The monospecific Srf I activity fractions deter mined by performing the assays described above/(substantially pure Srf I) were pooled and dialyzed to Buffer E (10 mM Tris-HCl at pH 8.0, 10 mM beta-mercaptoethanol, 5 mM EDTA, 40 mM KCl, 10 mM ammonium sulfate, 5% glycerol, 0.1% Triton X-100).

The dialyzed endonuclease was subsequently loaded onto a Mono Q (strong anionic exchanger based on monodisperse hydrophilic polymer particles, Pharmacia) column and washed with two column volumes of Buffer E. The immobilized endonuclease was eluted with a KCl gradient (0 to 0.3 M). FPLC fractions eluted from the Mono Q columns were collected into vials containing 100 $\mu$g/ml BSA and assayed as described above.

After chromatography on the Mono Q column above, the fractions containing Srf I activity (substantially pure Srf I) were pooled and dialyzed into Buffer F containing 10 mM KPO$_4$ at pH 7.0, 10 mM beta-mercaptoethanol, 1 mM EDTA and 0.1 M NaCl. The dialyzed endonuclease was then applied onto a 1.5×5 centimeter phosphocellulose column (Catalog Number, 407200, cellulose phosphate P-11 cationic exchanger, Whatman Biosystems Limited, Maidstone, Kent, England) that was pre-equilibrated with Buffer F. The column was then washed with two column volumes of Buffer F. The washed and immobilized endonuclease was eluted with a continuous salt gradient in Buffer F beginning with no NaCl up to 1 M NaCl. The fractions were collected into vials containing 100 μg/ml BSA. Fractions were then assayed for Srf I activity as described above.

Fractions containing Srf I activity were assayed for contamination by other nucleases and DNA binding proteins. Srf I activity-containing fractions, free of these contaminants, were determined to have endonuclease activity of 450,000 units (u). One unit is defined as the amount of restriction endonuclease required to cleave 1 μg of Adenovirus-2 DNA in one hour at 37° C. in a 50 μl reaction in 1× Universal Buffer as prepared in Example 1b. Thus, from 600 grams of Streptomyces rf cell paste, 450,000 units of activity were purified. The Srf I activity-containing fractions were then pooled into long term storage buffer (300 mM KCl, 10 mM Tris-HCl at pH 7.5, 10 mM beta-mercaptoethanol, 1 mM EDTA, 0.1% Triton X-100 50% glycerol, and 200 μg/ml BSA). The characterization of the resultant purified Srf I restriction endonuclease is described below.

2. Characterization of the Novel Srf I Restriction Endonuclease a. Determination of Molecular Weight of Srf I The molecular weight of Srf I was determined by both gel filtration methodology and by non-reducing SDS-PAGE. For the molecular weight determination by gel filtration, a Superose 12 column (cross-linked agarose, Pharmacia) was used following manufacturer's instructions. Briefly, the column was first equilibrated with a solution containing 0.5 M potassium chloride, 10 mM Tris-HCl, at pH 8.0, and 1 M EDTA. The molecular weight of Srf I was determined relative to the three molecular weight standards of beta-galactosidase (MW=116,000, Catalog Number 6-8511, Sigma), trypsin inhibitor (Mw=29,000, Catalog Number T-9767, Sigma) and carbonic anhydrase (Mw=20,000, Catalog Number C-2273, Sigma).

The void volume of the column ($V_O$) was first determined to be approximately 6.64 milliliters (mls) by loading the beta-galactosidase protein marker as it was excluded based on its size from the column. The protein peaks were detected by measuring the optical density of the collected fractions at a wavelength of 280 nanometers. The elution volumes for the other two molecular weight standards, trypsin inhibitor and carbonic anhydrase, and the FPLC purified Srf I restriction endonuclease prepared in Example 1c were then measured. Carbonic anhydrase and trypsin inhibitor eluted at the respective volumes of 11.93 and 13.99 mls. Srf I eluted at 10.6 mls.

The molecular weights of the protein standards were plotted on log-log paper on the Y-axis against the calculated elution volume (Ve) divided by the void volume ($V_E/V_O$) For example, for beta-galactosidase, the $V./V.=6.64$ divided by 6.64=1; similarly, for trypsin inhibitor, the $V_E/V_O=13.88$ divided by 6.64=2.09). Using line of best fit, Srf I was thus found to be approximately 55 kd by this methodology.

A second approach using sodium dodecylsulfate polyacrylamide gel electrophoresis (SDS-PAGE) was performed to determine the accuracy of the molecular weight determination of Srf I. A 12% Tris-glycine SDS-PAGE gel was prepared according to manufacturer's instructions catalog Number EC6005, Novex, Encinitas, Calif.) FPLC purified Srf I restriction endonuclease prepared in Example 1c was electrophoresed under non-reducing conditions in 1× Laemmli running buffer (10× Laemmli running buffer was prepared by admixing 303 grams of Tris base, 1442 grams of glycine, and 100 grams of SDS to 10 liters of water and pH was adjusted to 8.3) and compared to the following molecular weight standards obtained from, Bio-Rad (Richmond, Calif. Catalog Number 161–0304): rabbit muscle phosphorylase b (Mw=97,400); BSA (MW=66,200); hen egg white ovalbumin (MW=45,000); bovine carbonic anhydrase (MW=31,000); soybean trypsin inhibitor (MW=21,500); and hen egg white lysozyme (MW=14,400).

After electrophoresis, the gel was stained with Coomassie blue to reveal the migrated positions of the proteins in the gel. Under these conditions, Srf I ran slightly in front of (or faster than) BSA, but slower than hen egg white ovalbumin, and thus was determined to have a relative molecular weight of approximately 64 kd. Thus, the approximate molecular weight of FPLC purified Srf I restriction endonuclease was determined to be between 55 kd based on Superose 12 column gel filtration and 64 kd based on SDS-Page.

b. Determination of Cleavage Site Specificity of Srf I

1) Endonuclease Assays

Endonuclease assays were performed as described in Example 1b with FPLC purified Srf I restriction endonuclease on the following DNA substrates: Adenovirus-2, phage lambda (dam⁻, dcm⁻), pBR322, PhiX174, T7, SV40and T5. FIG. 1 shows the separate cleavage activity of Srf I on these DNA substrates. Srf I recognizes one site on Adenovirus-2 DNA producing two fragments of 27,571 and 8,366 base pairs long as shown in Lane 9 of FIG. 1. Srf I failed to cleave the remaining DNA substrates These results suggested a rare, probable octanucleotide base pair recognition sequence. Preliminary mapping and double digestion of Adenovirus-2 DNA with Srf I and with Bam HI and Spe I localized the site to within 200 base pairs. A computer scan (Beckman Microgenie) for all novel eight base palindromes was performed.

Within the scanned nucleotide region, five possible palindromic recognition sequences were identified which were consistent with the rarity of Srf I cleavage. Of these possible sequences, three eight base pair recognitions sequences were found along with one ten base pair and one twelve base pair palindrome. The ten and twelve base pair palindromes were both extensions of one of the three eight base pair palindromic sequences. PCR amplification as described below was used to generate three Adenovirus-2 DNA nucleotide sequence fragments, each containing one of the three palindromes of interest.

2) PCR of Octanucleotide Palindromes

PCR amplification of the three possible Srf I recognition sequences in Adenovirus-2 DNA was performed by first admixing 200 nanograms (ng) of Adenovirus-2 DNA with a PCR buffer consisting of 20 mM Tris-HCl at pH 8.8, 10 mM KCl, 6 mM $(NH_4)_2SO_4$, 1.5 MM $MgCl_2$ and 0.1% Triton X-100. To this admixture was admixed 0.25 mM each of dATP, dCTP, dGTP and dTTP (this corresponds to a 1/100 dilution of Stratagene's PCR grade dNTP mix, (Stratagene). Lastly, 250 ng in 1 μl of the selected synthetic oligonucleotides were admixed to form a PCR admixture. Eighty-two μl of distilled water was admixed to bring the PCR admixture to a final volume of 100 μl. The synthetic oligonucleotides used in the PCR reactions described below are shown in Table 1. The nucleotide sequence of each synthetic oligonucleotide having numerical designations from 873 to 878 is shown along with the corresponding SEQ ID NOs.

The nucleotide bases of the regions of Adenovirus-2 to which the synthetic oligonucleotides correspond are also indicated in the table immediately below the 5' and 3' bases in each oligonucleotide. The polarity of each oligonucleotide is indicated as a "+" and a "−" for sense and antisense primers, respectively.

TABLE 1

| DESIGNATION ID | SEQ ID NO | POLARITY | NUCLEOTIDE SEQUENCE AND CORRESPONDING NUCLEOTIDE REGION OF ADENOVIRUS-2 DNA |
|---|---|---|---|
| 873 | 2 | − | 5'- CAGAGTTAGGATCGCCTGAC-3'<br>27727                    27708 |
| 874 | 1 | + | 5'- GACGGGACATTTCAGATCGG-3'<br>27659                    27678 |
| 875 | 3 | − | 5'- CTCCACTGGTCATTCAGTCG-3'<br>27911                    27892 |
| 876 | 1 | + | 5'- CTCACCTGAAAATCAGAGGG-3'<br>27585                    27604 |
| 877 | 4 | − | 5'- TCGTCGTTGAGCTGAATACC-3'<br>27627                    27608 |
| 879 | 1 | + | 5'- CAGCGCCATTATGAGCAAGG-3'<br>27205                    27224 |

To determine the Srf I cleavage site in Adenovirus-2 DNA, pairs of sense and anti-sense primers from Table 1 were admixed in three separate reactions to form three separate PCR fragments, A, B, and C, corresponding to a region of Adenovirus-2 DNA from nucleotide base number 27205 through 27911 shown in FIG. 4 and listed in Sequence Listing (SEQ ID NO 1).

To amplify fragment A, primers 874 and 875 were admixed. If Srf cleaved the resultant Fragment A between nucleotide base number 27727 and 27728, the resultant fragments would be 184 base pairs (bp) and 68 bp. To amplify fragment B, primers 873 and 876 were admixed. If Srf I cleaved the resultant Fragment B between nucleotide base numbers 27657 and 27658, the resultant fragments would be 70 bp and 72 bp. To amplify Fragment C, primers 877 and 878 were admixed. If Srf I cleaved the resultant Fragment C between nucleotide base numbers 27571 and 27572, the resultant fragments would be 366 bp and 56 bp.

The separate PCR admixtures described above were heated for 5 minutes at 100° C., then cooled for 5 minutes at 53° C. followed by centrifugation for 30 seconds. Three μl of *Pyrococcus furiosus* DNA Polymerase (Stratagene) were then admixed with each reaction admixture to initiate the amplification reaction. Thirty rounds of amplification were performed on a Perkin-Elmer Cetus Thermal Cycler, each round consisting of 75 seconds at 72° C., 75 seconds at 96° C., 60 seconds at 53° C. followed by ten minutes at 72° C. The amplified reaction products were then maintained overnight at 4° C. The resultant PCR products were then digested with Srf I and electrophoresed on a 10% native polyacrylamide gel.

Figure 2:
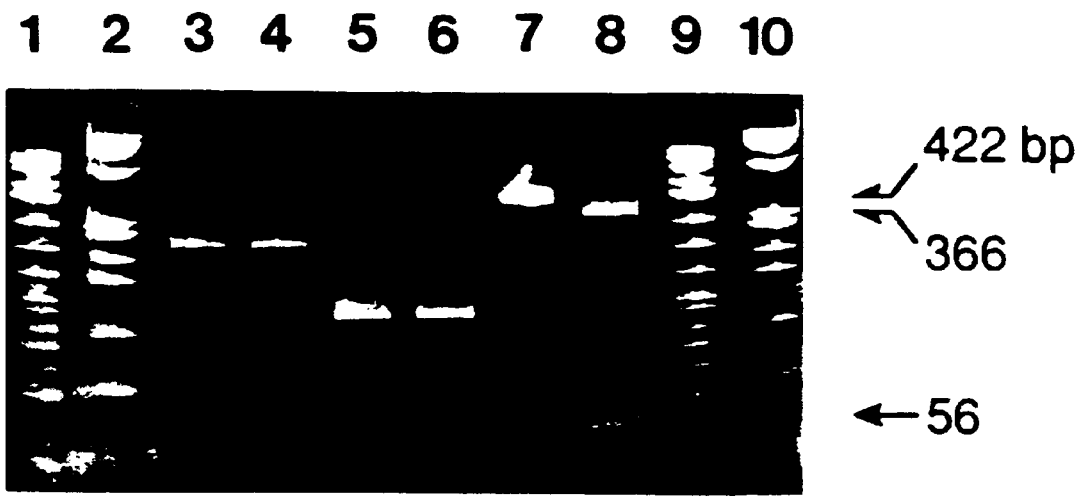
FIG. 2 illustrates the cleavage of PCR amplified Adenovirus-2 regions containing putative recognition sequences. Lanes: 1 and 9, Hae III digest of PhiX174 as a size marker; 2 and 10, Hinf I digest of PhiX174 as a size marker; 3, PCR fragment A (Ad-2 nucleotide (nt) 27650 to nt 2791 1); 4, Fragment A maintained with Srf I; 5, Fragment B (Ad-2 nt 27585 to nt 27727); 6, Fragment B maintained with Srf I; 7, Fragment C (Ad-2 nt 27205 to nt 27627); 8, Fragment C maintained with Srf I. Restriction endonuclease activity was assayed by maintenance of each PCR fragment in 1× Universal Buffer (Stratagene) (10× Universal Buffer: 1M KAc, 250 mM Tris-Acetate, pH 2.6, 100 mM MgAc, 5 mM beta-mercaptoethanol, and 100 μg/ml bovine serum albumin (BSA)) with 0 or 1 U of Srf I at 37° C. for-3 hours. Restriction fragments were analyzed by electrophoresis in a 10% polyacrylamide gel prepared in TBE buffer.

The results of the digestion of the palindromic octanucleotide PCR products are shown in FIG. 2, Lane 8, where cleavage occurred at nucleotide base number 27571 and the recognition sequence of Srf I was thus identified as the eight nucleotide base palindrome 5' GCCCGGGC 3' in fragment C having the nucleotide region from 27205 to 27627 of Adenovirus-2 DNA Srf I cleaved the palindrome after the third C resulting in two fragments of 366 and 56 base pairs as shown in Lane 8. The fragments A and B were not digested by Srf I confirming the results seen with Fragment C.

3) Primed Synthesis Reaction

To confirm the cleavage site within the Srf I recognition sequence, the cleavage of a primed synthesis reaction was performed. pBluescript II SK+ (Stratagene), containing a recognition sequence for Srf I in its multicloning site, was used as a template. To accomplish this construction, a linker containing the Srf I recognition sequence determined above was cloned into the EcoR V site of the polylinker of pBluescript II SK+ (Stratagene) to form a plasmid template, pSMSrr 1. One hundred nanograms (ng) of EcoR V-cleaved pBluescript II Sk+ were admixed with 50 ng of Srf I linker (double stranded 5'-CAAGCCCGGGCTTG-3'-SEQ ID NO 5) in 1× ligation buffer (50 mM TrisHCl at pH 7.5, 7 mM MgCl$_2$, 1 mM DTT and (1 mM ATP) and 4 Weiss U T4 DNA ligase in a reaction volume of 25 μl. The ligation admixture was maintained for 16 hours at 15° C. Ligase was then inactivated by heating for 15 minutes at 72° C. The ligation reaction was then admixed with 6 U EcoR V and one-tenth volume of EcoR V cleavage buffer (10 mM DTT, Tris-HCl at pH 7.7, 150 mM NaCl, 10 mM MgCl$_2$, 1 mM DTI and 100 μg/ml BSA) to form a reaction admixture. The admixture was then maintained for 30 minutes at 37° C. to form EcoRV cleavage products. EcoRV cleavage linearizes any wild-type pBluescript II Ski which has self-ligated and does not contain the Srf I linker.

The EcoRV cleaved ligation was then used to transform *E. coli* strain SURE™ (Stratagene). Plasmid DNA was propagated overnight in SURE™ cells for cesium chloride gradient purification of the plasmid, pSMSrf I. The resultant template was first denatured and then was admixed with T7 DNA polymerase, the M13 (−20) primer, previously end-labeled with $^{35}$S-ATP, and the four deoxynucleotides, dATP, dCTP, dGTP and dTTP. The reaction was maintained for five minutes at 37° C. to extend the primer beyond the nucleotide recognition site. The reaction product was subsequently cleaved with Srf I as prepared in Example 1c and then divided into four equal portions. Two of the resultant cleavage reactions were admixed with the four deoxynucleotides described above and maintained for ten minutes at 37° C. with 6 U Klenow fragment of DNA polymerase I to fill-in any overhang generated by restriction enzyme cleavage. One of the filled-in reactions and one of the control reactions were admixed with an equal volume of the standard sequencing "C" reaction and loaded next to the control reactions not mixed with C. Standard dideoxy sequencing reactions were carried out in parallel using T7 polymerase. All reaction mixtures were electrophoresed on a 8% denaturing polyacrylamide gel for DNA sequencing.

Figure 3:
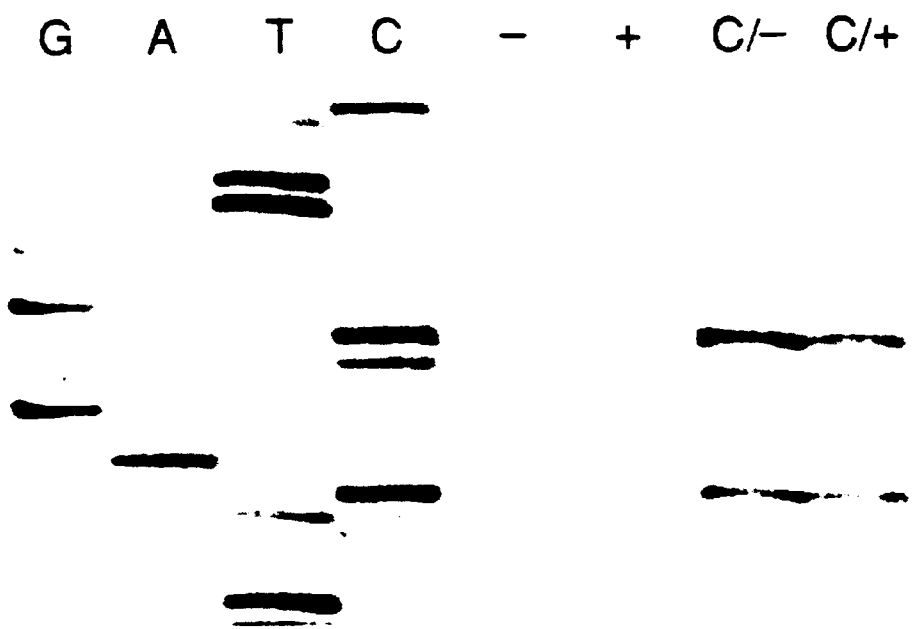
FIG. 3 illustrates the determination of the Srf I cleavage specificity by a primed synthesis reaction performed as described in Example 2b. Lanes: G, A, T and C, the sequencing ladders through the Srf I recognition sequence; 5, Srf I-cleaved extension reaction; 6, Klenow fill-in reaction of Srf I-cleaved extension reaction; 7, Srf I-cleaved extension reaction plus "C" dideoxy sequencing reaction; 8, Klenow fill-in reaction of Srf I-cleaved extension reaction plus "C" dideoxy sequencing reaction. Standard dideoxy sequencing reactions as described by Sanger et al., *Proc. Natl. Acad. Sci.. USA*, 74:5463–5467 (1977), were performed using a pBluescript 11 SK+ derivative (pSMSrf I), with an insert containing a Srf I cleavage site as template, the M13(−20) primer and T7 DNA polymerase. Four μl of each sequencing reaction were loaded onto an 8% denaturing reactions was generated by extension of the M13(−20) primer with the four deoxynucleotides including α$^{35}$-S-dATP and T7 DNA polymerase on plasmid, pSMSrf I, template. After splitting the extension reactions, cleavage reactions were conducted using 6 U of Srf I for 15 minutes at 37° C. Four μl of each cleavage reaction ± Klenow fill-in (Klenow fill-in kit, Stratagene) were loaded per lane. Two μl of cleavage reaction ± Klenow fill-in were admixed with 2 μl "C" sequencing reaction to illustrate gel shift of cleavage products.

An autoradiograph of the primed synthesis reaction used to determine the cleavage site of Srf I is shown in FIG. 3. Lane 5 shows that the extended product was cleaved with Srf I producing a fragment which migrated between the second and the third C of the recognition sequence 5'-GCCCGGGC-3'. Because cleavage of the Fragment C produced by PCR in Example 2b2) above suggested cleavage after the third C, it was suspected that cleavage products were running slightly differently from the dideoxy sequencing reactions due to reaction buffer difference.

Mixing experiments described above confirmed this result. When cleavage reactions ± Klenow fill-in were admixed with "C" sequencing reactions, the cleavage products ran with the third C in the sequence as shown in Lanes 7 and 8, respectively, of FIG. 3. That Srf I cleaved after the third C leaving blunt ends was demonstrated by the migration of the cleavage products ± Klenow fill-in as shown in Lanes 5 and 6, respectively. No difference in migration was observed after Klenow fill-in of Srf I cleavage products.

These results indicate that Srf I cleaved the DNA leaving blunt ends. The recognition sequence and cleavage site indicated by the asterisk are thus: 5'GCCC'GGGC-3'.

Incorporation by Reference

All patents, patent applications, and publications cited herein are incorporated by reference.

Equivalents

The foregoing written specification is considered to be sufficient to enable one skilled in the art to practice the invention. Indeed, various modifications of the above-described makes for carrying out the invention which are obvious to those skilled in the field of molecular biology or related fields are intended to be within the scope of the following claims.

What is claimed is:

1. A purified restriction endonuclease produced by a host cell transformed with an expression vector comprising a polynucleotide in functional combination with a promoter sequence, wherein said polynucleotide encodes a restriction endonuclease having a specificity for, and a cleavage site in a double stranded nucleotide sequence represented by the formula:

```
5'GCCC*GGGC3'
3'CGGG*CCCG5'
``` wherein G and C respectively represent the nucleotides guanine and cytosine and * represents the Srf I cleavage site in each strand of said double stranded nucleotide sequence.

2. A purified restriction endonuclease according to claim 1 wherein the polynucleotide was originally isolated from a Streptomyces species.

3. A purified restriction endonuclease according to claim 2, wherein the restriction endonuclease is Srf I.

* * * * *

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
    (A) LENGTH: 707 base pairs
    (B) TYPE: nucleic acid
    (C) STRANDEDNESS: unknown
    (D) TOPOLOGY: unknown (ii) MOLECULE TYPE: DNA (xi) SEQUENCE DESCRIPTION: SEQ ID NO:1:

```
CAGCGCCATT ATGAGCAAGG AAATTCCCAC GCCCTACATG TGGAGTTACC AGCCACAAAT      60
GGGACTTGCG GCTGGAGCTG CCCAAGACTA CTCAACCCGA ATAAACTACA TGAGCGCGGG     120
ACCCCACATG ATATCCCGGG TCAACGGAAT CCGCGCCCAC CGAAACCGAA TTCTCCTCGA     180
ACAGGCGGCT ATTACCACCA CACCTCGTAA TAACCTTAAT CCCCGTAGTT GGCCCGCTGC     240
CCTGGTGTAC CAGGAAAGTC CCGCTCCCAC CACTGTGGTA CTTCCCAGAG ACGCCCAGGC     300
CGAGGTTCAG ATGACTAACT CAGGGGCGCA GCTTGCGGGC GGCTTTCGTC ACAGGGTGCG     360
GTCGCCCGGG CAGGGTATAA CTCACCTGAA AATCAGAGGG CGAGGTATTC AGCTCAACGA     420
CGAGTCGGTG AGCTCCTCTC TTGGTCTCCG TCCGACGGG ACATTTCAGA TCGGCGGCGC      480
TGGCCGCTCT TCATTTACGC CCCGTCAGGC GATCCTAACT CTGCAGACCT CGTCCTCGGA     540
GCCGCGCTCC GGAGGCATTG GAACTCTACA ATTTATTGAG GAGTTCGTGC CTTCGGTTTA     600
CTTCAACCCC TTTTCTGGAC CTCCCGGCCA CTACCCGGAC CAGTTTATTC CCAACTTTGA     660
CGCGGTGAAA GACTCGGCGG ACGGCTACGA CTGAATGACC AGTGGAG                   707
```

(2) INFORMATION FOR SEQ ID NO:2:

(i) SEQUENCE CHARACTERISTICS:
    (A) LENGTH: 20 base pairs
    (B) TYPE: nucleic acid
    (C) STRANDEDNESS: unknown
    (D) TOPOLOGY: unknown (ii) MOLECULE TYPE: DNA (genomic)

(xi) SEQUENCE DESCRIPTION: SEQ ID NO:2:

```
CAGAGTTAGG ATCGCCTGAC                                                  20
```

(2) INFORMATION FOR SEQ ID NO:3:

(i) SEQUENCE CHARACTERISTICS:
    (A) LENGTH: 20 base pairs
    (B) TYPE: nucleic acid
    (C) STRANDEDNESS: unknown
    (D) TOPOLOGY: unknown (ii) MOLECULE TYPE: DNA (genomic)

(xi) SEQUENCE DESCRIPTION: SEQ ID NO:3:

CTCCACTGGT CATTCAGTCG                                             20

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:4:

TCGTCGTTGA GCTGAATACC                                             20

(2) INFORMATION FOR SEQ ID NO:5:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:5:

CAAGCCCGGG CTTG                                                   14

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:6:

GACGGGACAT TTCAGATCGG                                             20

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:7:

CTCACCTGAA AATCAGAGGG                                             20

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: unknown
        (D) TOPOLOGY: unknown

```
(ii) MOLECULE TYPE: DNA (genomic)

(xi) SEQUENCE DESCRIPTION: SEQ ID NO:8:

CAGCGCCATT ATGAGCAAGG                                         20
```